United States Patent
Delury et al.

(10) Patent No.: US 11,752,235 B2
(45) Date of Patent: Sep. 12, 2023

(54) COLLAGEN/ORC DRESSING ENCAPSULATED WITHIN A BIORESORBABLE ENVELOPE

(71) Applicant: SYSTAGENIX WOUND MANAGEMENT, LIMITED, West Sussex (GB)

(72) Inventors: Craig Delury, Gargrave (GB); Alexander Waite, Keighley (GB)

(73) Assignee: KCI Licensing, Inc., San Antonio, TX (US)

(*) Notice: Subject to any disclaimer, the term of this patent is extended or adjusted under 35 U.S.C. 154(b) by 1247 days.

(21) Appl. No.: 16/325,658

(22) PCT Filed: Aug. 14, 2017

(86) PCT No.: PCT/US2017/046822
§ 371 (c)(1),
(2) Date: Feb. 14, 2019

(87) PCT Pub. No.: WO2018/035063
PCT Pub. Date: Feb. 22, 2018

(65) Prior Publication Data
US 2019/0201574 A1 Jul. 4, 2019

Related U.S. Application Data

(60) Provisional application No. 62/375,696, filed on Aug. 16, 2016.

(51) Int. Cl.
| | | |
|---|---|---|
| *A61L 15/64* | (2006.01) | |
| *A61L 15/44* | (2006.01) | |
| *A61L 15/28* | (2006.01) | |
| *A61L 26/00* | (2006.01) | |
| *A61L 15/32* | (2006.01) | |
| *A61L 15/42* | (2006.01) | |
| *A61F 13/539* | (2006.01) | |
| *A61F 13/15* | (2006.01) | |
| *A61F 13/00* | (2006.01) | |
| *C08L 5/08* | (2006.01) | |
| *C08L 1/04* | (2006.01) | |
| *A61F 13/511* | (2006.01) | |
| *A61F 13/53* | (2006.01) | |

(52) U.S. Cl.
CPC ........ *A61L 15/64* (2013.01); *A61F 13/00012* (2013.01); *A61F 13/00017* (2013.01); *A61F 13/15252* (2013.01); *A61F 13/539* (2013.01); *A61L 15/28* (2013.01); *A61L 15/32* (2013.01); *A61L 15/325* (2013.01); *A61L 15/425* (2013.01); *A61L 15/44* (2013.01); *A61L 26/0009* (2013.01); *A61L 26/0085* (2013.01); *A61F 2013/00221* (2013.01); *A61F 2013/15878* (2013.01); *A61F 2013/51147* (2013.01); *A61F 2013/530802* (2013.01)

(58) Field of Classification Search
CPC ........ A61L 15/64; A61L 15/28; A61L 15/325; A61L 15/425; A61L 15/44; A61L 26/0009; A61L 26/0085; A61F 13/00012; A61F 13/00017; A61F 13/539
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(Continued)

*Primary Examiner* — Alma Pipic

(57) ABSTRACT

Wound dressing compositions comprising of a bioresorbable sponge encapsulated within a polysaccharide envelope. The bioresorbable sponge is preferably comprised of collagen and oxidised regenerated cellulose. The outer polysaccharide envelope is preferably comprised of chitosan. The outer polysaccharide envelope functions to modulate the rate at which the bioresorbable sponge breaks down within a wound.

12 Claims, 2 Drawing Sheets

(56) References Cited

U.S. PATENT DOCUMENTS

| | | |
|---|---|---|
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0149182 A1 | 7/2006 | Cullen et al. |
| 2007/0264460 A1 | 11/2007 | Tredici |
| 2014/0142523 A1* | 5/2014 | Steinbaugh |

FOREIGN PATENT DOCUMENTS

| | | |
|---|---|---|
| AU | 755496 B2 | 12/2002 |
| CA | 1124951 A | 6/1982 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0 562 864 A1 * | 9/1993 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2314842 A | 1/1998 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 98/00180 * | 1/1998 |
| WO | 99/13793 A1 | 3/1999 |
| WO | 2004/026200 A2 | 4/2004 |
| WO | 2015/140565 A1 | 9/2015 |

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.

(56) References Cited

OTHER PUBLICATIONS

Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion in International Application No. PCT/US2017/046822, dated Feb. 22, 2018 (16 pages).

* cited by examiner

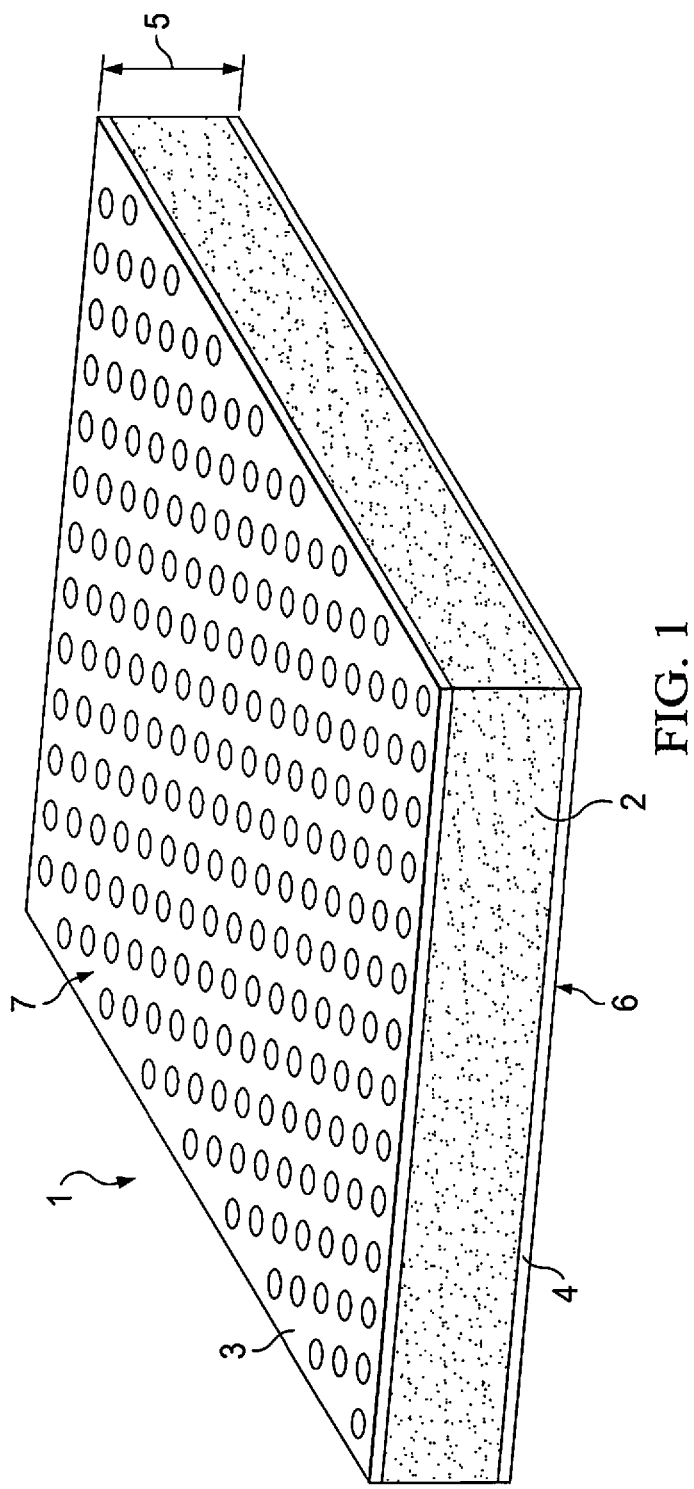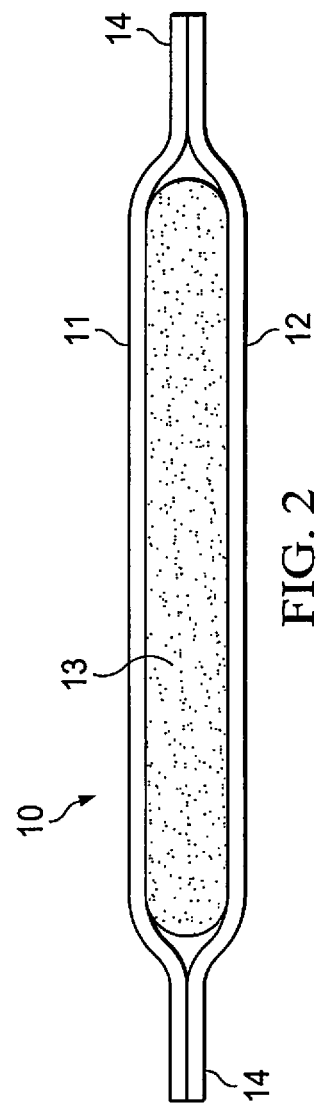
FIG. 1
FIG. 2

COLLAGEN/ORC DRESSING ENCAPSULATED WITHIN A BIORESORBABLE ENVELOPE

TECHNICAL FIELD

The present application is a US national phase application under 35 USC § 371 of International Application No. PCT/US2017/046822, filed on Aug. 14, 2017, which claims the benefit, under 35 U.S.C. § 119(e), of U.S. Provisional Patent Application Ser. No. 62/375,696, entitled "COLLAGEN/ORC DRESSING ENCAPSULATED WITHIN A BIORESORBABLE ENVELOPE," filed Aug. 16, 2016. Each application is incorporated herein by reference for all purposes.

The present technology relates to compositions and devices, including wound dressings, for application to wounds.

INTRODUCTION

A wide variety of materials and devices, generally characterized as "wound dressings," are known in the art for use in treating an injury or other disruption of tissue. Such wounds may be the result of trauma, surgery, or disease, and affect skin or other tissues. In general, dressings may control bleeding, absorb wound exudate, ease pain, assist in debriding the wound, protect wound tissue from infection, modulate proteases, or otherwise promote healing and protect the wound from further damage.

A variety of materials are known in the art for use in wound dressings which include synthetic or natural materials that offer a range of chemical and physical characteristics. These dressings can include various active components, such as antimicrobials enzymes, structural proteins, growth factors and other materials that aid in the healing of wounds and regeneration of tissue at wound sites. Such dressings and materials can be highly effective in the treatment of wounds, but may be subject to issues regarding the biocompatibility of materials, bioavailability of therapeutic substances, ability to absorb wound exudate, wound protection, efficacy of materials over an extended time of use, storage stability, ease of clinical use, and cost. Accordingly, there remains a need for improved wound dressings addressing one or more of such characteristics as well as providing other benefits relative to wound dressings among those known in the art.

SUMMARY

The present technology provides wound dressings comprising collagen, oxidized regenerated cellulose (ORC) and a polysaccharide polymer. In various embodiments, the dressings comprise an absorbent structure, preferably a bioresorbable sponge, having a wound-facing surface, and a bioresorbable top sheet covering the wound-facing surface. The absorbent structure central sponge comprises the ORC and collagen, and the top sheet comprises the polysaccharide polymer, such as chitosan. In a preferred embodiment, the absorbent structure may further comprise a structural protein, such as collagen. For example, the weight ratio ORC:collagen may be from about 1:1 to about 9:1.

In various embodiments, the dressing also comprises a bottom sheet comprised of a polysaccharide polymer. The bottom sheet and the top sheet may be bonded to substantially encapsulate the bioresorbable sponge. For example, the edges of the top sheet and the edges of the bottom sheet extend beyond the surface of the absorbent structure, and the edges of the top sheet and the edges of the bottom sheet are bonded by heat sealing. The top sheet may be fluid permeable; for example, comprising a plurality of perforations.

The wound dressings may comprise a therapeutic wound healing agent incorporated in one or more of the top sheet, bottom sheets, and the absorbent structure. Such agents may include non-steroidal anti-inflammatory drug, steroids, anti-inflammatory cytokines, anesthetics, antimicrobial agents, growth factors, and mixtures thereof.

The present technology also provides methods of treating wounds, comprising applying to a surface of the wound a dressing having a wound-facing surface, the dressing comprising an absorbent structure (e.g., bioresorbable sponge) that is encapsulated in an envelope comprising a bioresorbable polymer. The envelope may have perforations in fluid communication with the wound-facing surface of the absorbent structure. In various embodiments, the absorbent structure is fully or significantly degraded from about 1 day to about 7 days after the dressing is applied to the wound, depending on exudate levels and conditions within the wound. In various embodiments, the top sheet and bottom sheet may reduce this degradation rate.

DRAWINGS

FIG. 1 is a perspective view of a wound dressing according to the present technology.

FIG. 2 is a side view of a wound dressing according to the present technology.

Figure 3:
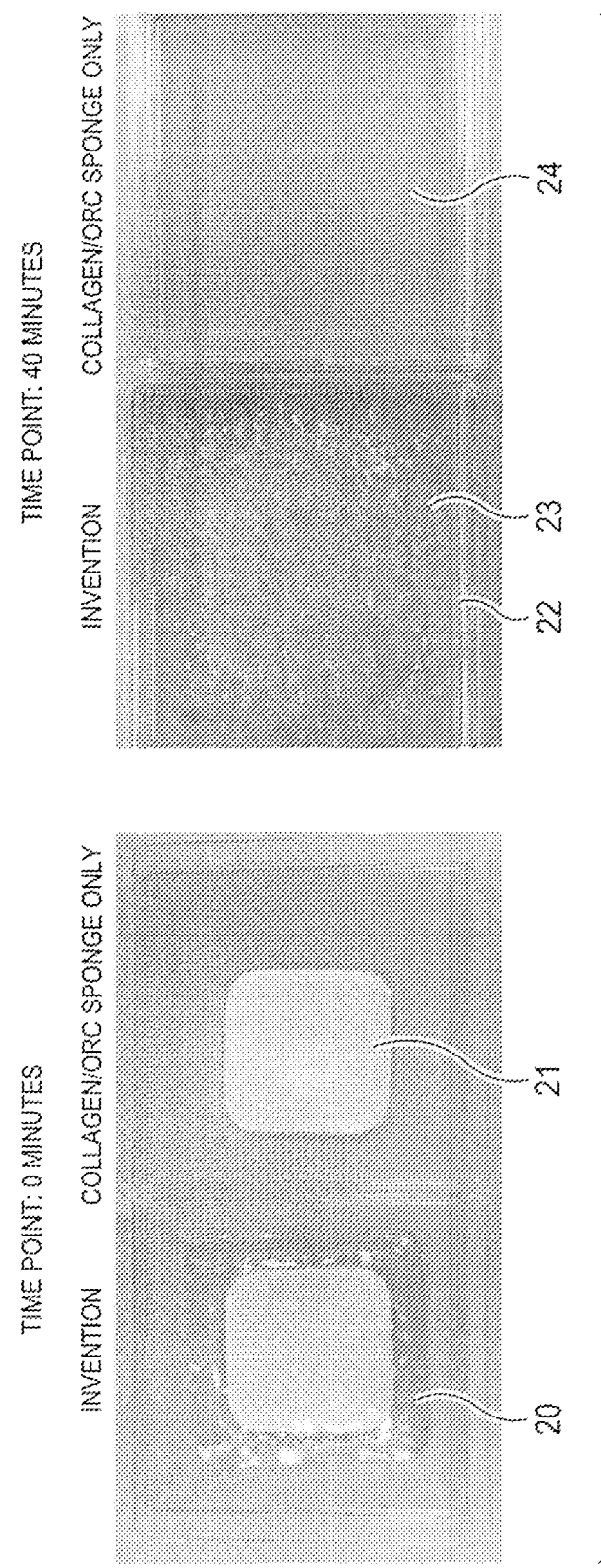

FIG. 3 consists of two photographs of a wound dressing of the present technology, and a control test material, incubated in a simulated wound fluid with enzyme (collagenase).

It should be noted that the figures set forth herein are intended to exemplify the general characteristics of materials and methods among those of the present technology, for the purpose of the description of certain embodiments. The figures may not precisely reflect the characteristics of any given embodiment, and are not necessarily intended to define or limit specific embodiments within the scope of this technology.

DESCRIPTION OF EXAMPLE EMBODIMENTS

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. In particular, the following description sets forth example embodiments and otherwise provides information that enables a person skilled in the art to make and use the subject matter set forth in the appended claims, but may omit certain details already well-known in the art. The following description is, therefore, to be taken as illustrative and not limiting. A non-limiting discussion of terms and phrases intended to aid understanding of the present technology is provided at the end of this Detailed Description.

The present technology provides wound dressings and compositions useful in wound dressing compositions. Preferably, the materials used in such dressings are physiologically acceptable, commensurate with a reasonable risk/benefit ratio when used in the manner of this technology according to sound medical practice.

In various embodiments the dressings comprise oxidized regenerated cellulose, collagen and a polysaccharide polymer. In various embodiments, the dressings comprise a bioresorbable sponge having a wound-facing surface and comprising the oxidized regenerated cellulose and collagen, and a bioresorbable top sheet covering the wound-facing surface and comprising the polysaccharide polymer.

As referred to herein, a resorbable material or structure is a material which is destroyed, disrupted, disappears, or dissolved upon exposure to physiological fluids or processes when used in a method of the present technology, such as when applied to wound tissue. It is understood that such resorption may occur as a result of chemical or physical processes, or both. For example, in various embodiments, the absorbent structure (bioresorbable sponge) dissolves in about 8 hours, in about 5 hours, in about 3 hours, in about 2 hours, in about 1 hour, in about 30 minutes, or less, when incubated with simulated wound fluid with collagenase enzyme (0.1 mg/ml) at a temperature of about 37° C. In various embodiments, the dressing is bioresorbable such that it is not necessary for the wound dressing to be removed from the tissue to which it is applied during a method of the present technology.

Absorbent Structure

The wound dressing compositions of the present technology comprise absorbent structure comprising a bioresorbable freeze dried collagen/ORC pad, e.g., a "sponge," that forms a gel when contacted with an aqueous medium, such as water, blood or wound exudate. The wound dressing absorbent structure comprises oxidized regenerated cellulose, more preferably oxidized regenerated cellulose (ORC). Oxidized regenerated cellulose may be produced by the oxidation of cellulose, for example with dinitrogen tetroxide. This process converts primary alcohol groups on the saccharide residues to carboxylic acid groups, forming uronic acid residues within the cellulose chain. The oxidation may not proceed with complete selectivity, and as a result hydroxyl groups on carbons 2 and 3 may be converted to the keto form. These ketone units introduce an alkali labile link, which at pH 7 or higher initiates the decomposition of the polymer via formation of a lactone and sugar ring cleavage. As a result, oxidized cellulose is biodegradable and bioabsorbable under physiological conditions.

The preferred oxidized cellulose for practical applications is oxidized regenerated cellulose (ORC) prepared by oxidation of a regenerated cellulose, such as rayon. ORC may be manufactured by the process described in U.S. Pat. No. 3,122,479, Smith, issued Feb. 24, 1964, incorporated herein by reference. ORC is available with varying degrees of oxidation and hence rates of degradation. The ORC may be, for example, in the form of solid fibers, sheet, sponge or fabric. In various embodiments, the ORC comprises insoluble fibers, including woven, non-woven and knitted fabrics. In other embodiments, the ORC is in the form of water-soluble low molecular weight fragments obtained by alkali hydrolysis of ORC.

ORC may be present in the composition at any level appropriate to result in the desired ability to modulate proteases, absorbency, and/or rheological characteristics of the wound dressing composition. In general, the ORC may be present in the absorbent structure at a level of from about 10% to about 50%, or from about 30% to about 60%, and preferably from about 40% to about 50% (preferably 45% ORC to 55% collagen). (Unless otherwise indicated, all percentages herein are by weight of the absorbent structure.)

In various embodiments, the absorbent structure further comprises a structural protein comprising collagen. In various embodiments, the protein consists essentially of collagen. The collagen may be obtained from any natural source. The collagen may be Type I, II or III collagen, or may also be chemically modified collagen, for example an atelocollagen obtained by removing the immunogenic telopeptides from natural collagen. The collagen may also comprise solubilised collagen or soluble collagen fragments having molecular weights in the range of from about 5,000 to about 100,000, preferably from about 5,000 to about 50,000, obtained, for example, by pepsin treatment of natural collagen. In various embodiments, the collagen is obtained from bovine corium that has been rendered largely free of non-collagenous components. Such non-collagenous components include fat, non-collagenous proteins, polysaccharides and other carbohydrates, as described in U.S. Pat. No. 4,614,794, Easton et al., issued Sep. 30, 1986 and U.S. Pat. No. 4,320,201, Berg et al., issued Mar. 16, 1982, incorporated by reference herein. In various embodiments, the absorbent structure may also comprise a second structural protein selected from the group consisting of fibronectin, fibrin, laminin, elastin, and gelatin.

The collagen may be present in the wound dressing at a level of from about 40% to about 90%, or from about 45% to 65%, or preferably from about 50% to 60% (preferably 55%). In various embodiments, the bioresorbable sponge comprises a mixture of ORC and structural protein (e.g., collagen), wherein the weight ratio of ORC:collagen is from about 1:1 to about 1:10.

In various embodiments, the absorbent structure may comprise a hydrogel, such as hyaluronic acid or salt thereof.

In various embodiments, the absorbent structures preferably comprise less than about 1% water. Preferably the absorbent structures are freeze dried. Freeze drying, or lyophilization, methods useful herein include those known in the art.

Top Sheet

The wound dressings of the present technology also comprise a top sheet covering the wound-facing surface of the absorbent structure, as further discussed below. The top sheet comprises a resorbable polysaccharide. For example, polysaccharide material may be selected from the group consisting of alginates, chitosan, chitin, guar gums, starch, starch derivatives, ß-Glucans, cellulose, cellulose derivatives, glycosaminoglycans, chondroitin sulfate, heparin sulfate, pectins, and mixtures thereof.

In some embodiments, the resorbable polysaccharide comprises, or is, chitosan. Chitosan is derived from the natural biopolymer, chitin, which is composed of N-acetyl-D-glucosamine units. Chitin may be extracted from the outer shell of shrimps and crabs in known fashion. The chitin is then partially deacetylated, for example by treatment with 5M-15M NaOH, to produce chitosan. Complete deacetylation of the chitin is not a practical possibility, but preferably the chitosan is at least 50% deacetylated, more preferably at least 75% deacetylated. Chitosan in the free base form is swellable but not substantially soluble in water at near-neutral pH, but soluble in acids due to the presence of ammonium groups on the chitosan chain. The solubility of the chitosan may be reduced by cross-linking, for example with epichlorhydrin. Typically, the average molecular weight of the chitosan as determined by gel permeation chromatography is from about $10^5$ to about $10^6$. Chitosan may be incorporated into the top sheet in any appropriate physical forms, for example, as a film/membrane; sponge; or fiber.

In various embodiments, the top sheet comprises from about 80% to about 100%, or from about 25% to about 75% of the resorbable polysaccharide (e.g., chitosan), by weight of the top sheet. In some embodiments, the solution used to generate the top sheet material has a solids content of from about 1% to about 10%, preferably from about 1% to about 5%, more preferably from about 1% to about 2%. The top sheet may be made by any of a variety of suitable methods, including casting or molding an aqueous solution comprising the resorbable polysaccharide into a substantially planar sheet structure (as further described below), and drying. The aqueous solution may be generated through combining chitosan with 0.05M Acetic acid at 1.5% w/v with continuous stirring until the solution becomes homogenous. A plasticizer (such as glycerol) may be added so that the resulting film material is flexible. The aqueous solution is then dried at 37° C. in a tray for 24 hours to generate a film material.

In various embodiments, the top sheet modulates the exposure of the absorbent structure to tissue and tissue fluids (for example, tissue exudate comprising bacterial collagenase), so as to control the bioresorption of the of the collagen/ORC sponge. Such modulation may be as effected by the chemical composition of the top sheet (e.g., the resorbability of the materials comprising the top sheet) or the physical properties of the top sheet, or both. Accordingly, in various embodiments, the top sheet is resorbable. The rate of resorption may be controlled, however, so as to delay exposure of the absorbent structure to physiological fluids from the wound site or other tissue to which the wound dressing is applied. In some embodiments, the top sheet is intact or exhibits slight degradation when incubated with simulated wound fluid containing enzyme (collagenase at 0.1 mg/ml) at a temperature of about 37° C.

In some embodiments, the top sheet comprises a perforation, preferably a plurality of perforations. For example, the wound dressing may have a perforation density of about 4/cm$^2$, and the perforations have an average diameter of from about 0.02 cm to about 0.4 cm.

Optional Components:

The wound dressing compositions may comprise one or more optional materials. Such optional components may include, for example, preservatives, stabilizing agents, plasticizers, matrix strengthening materials, dyestuffs, and actives. For example, the absorbent structure may contain other materials that affect the chemical or physical properties of the absorbent structure, such as resorbabilty, rheology, pliability, and tear resistance The wound dressing composition may contain a plasticizer, such as glycerol or other polyhydric alcohol. If present, the plasticizer is present at a level of from about 0.05% to about 5%, preferably 0.1-0.5% by weight.

The wound dressing composition may also comprise one or more active materials which aid in wound healing. For example, such active materials may be present in one or more of the absorbent structure, the top sheet, and bottom sheet. Actives include non-steroidal anti-inflammatory drugs (e.g. acetaminophen), steroids, antibiotics, antiseptics (e.g., silver and chlorhexidine), and growth factors (e.g. fibroblast growth factor or platelet derived growth factor). Such actives may be included in the absorbent structure, the top sheet, or both. If present, actives are present in "safe and effective" amounts. Such safe and effective amounts are sufficient to have the desired effect (e.g., antimicrobial activity), without undue adverse side effects (such as toxicity, irritation, or allergic response), commensurate with a reasonable benefit/risk ratio when used in the manner of this technology. The specific safe and effective amount of an active may vary with the active and other factors such as the physical form of the active, the type and quantity of other materials in the composition, the intended use, and the physical condition of the subject on whom the wound dressings are used. In general, such actives are optionally present at a level of from about 0.1% to about 10%.

For example, the wound dressing may comprise an antimicrobial selected from the group consisting of tetracycline, penicillins, terramycins, erythromycin, bacitracin, neomycin, polymycin B, mupirocin, clindamycin and mixtures thereof. Antiseptics among those useful in the wound dressings include silver, chlorhexidine, polyhexamethylene biguanide, povidone iodine, triclosan, sucralfate, quaternary ammonium salts and mixtures thereof. In various embodiments, the wound dressings comprise silver, which may be in metallic form, in ionic form (e.g., a silver salt), or both. For example, the silver may be present in ionic form, such as in a complex with an anionic polysaccharide in the composition. In various embodiments, the wound dressing composition comprises a complex of silver and ORC (a "Silver/ORC Complex"). As referred to herein, such a complex is an intimate mixture at the molecular scale, preferably with ionic or covalent bonding between the silver and the ORC. The Silver/ORC Complex preferably comprises a salt formed between the ORC and Ag$^+$, but it may also comprise silver clusters or colloidal silver metal, for example produced by exposure of the complex to light. The complex of an anionic polysaccharide and silver contained in the materials of the present invention can be made by treating the ORC with a solution of a silver salt. In various embodiments, the silver salt is the salt of silver with a weak acid. The reaction of ORC and silver can be carried out in water or alcohol alone but is preferably carried out in mixtures of water and alcohols. Generally, the amount of silver in the Silver/ORC Complex may be from about 0.1% to about 50% by weight of the ORC, or from about 1% to about 40%, or about 2% to about 30% or from about 5% to about 25% by weight of the ORC. Silver/ORC complexes useful herein, and methods of producing such complexes, are described in U.S. Pat. No. 8,461,410, Cullen et al., issued Jun. 11, 2013, incorporated by reference herein. Similar processes are described in U.S. Pat. No. 5,134,229, Saferstein et al., issued Jul. 28, 1992, incorporated by reference herein. In various embodiments, the Silver/ORC Complex may be present in the wound dressing composition at a level of from about 1% to about 2%. For example, a dressing composition may comprise from about 1% to about 2% of a Silver/ORC Complex (by weight of the composition), wherein the Silver/ORC Complex comprises from about 20% to about 30% (e.g., about 25%) of silver by weight of the ORC.

In some embodiments, such as dressings comprising silver, the wound dressing compositions comprises a dyestuff, which is preferably light-absorbing in the visible region 400-700 nm. Such dyestuffs may be operable to photochemically trap generated free radicals that could otherwise react with the silver in the present compositions, acting as photochemical desensitisers. In various embodiments, the antioxidant dyestuff is selected from the group consisting of aniline dyes, acridine dyes, thionine dyes, bis-naphthalene dyes, thiazine dyes, azo dyes, anthraquinone dyes, and mixtures thereof. For example, the antioxidant dyestuff may be selected from the group consisting of gentian violet, aniline blue, methylene blue, crystal-violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, methylene green, and mixtures thereof. If present, the dyestuff may be present at a level of about 0.05% to about 5%, typically about 0.2% to about 2%.

Wound Dressing Structures

The present technology provides wound dressings comprising an absorbent structure (e.g., bioresorbable sponge) and a top sheet, as described above. In general, with reference to FIG. 1, such dressings 1 comprise an absorbent structure 2 of the present technology. The absorbent structure 2 is preferably in substantially sheet form, i.e., having a generally planar structure with two opposite planar surfaces and a depth (or thickness) 5 orthogonal to the planar surfaces.

The wound dressing has a wound-facing surface 7 and an opposite back surface 6. Similarly, the absorbent structure has corresponding wound-facing and back surfaces. The wound-facing surface may have a surface area of from about 1 cm$^2$ to about 400 cm$^2$. Such "planar" surfaces may have a variety of shapes, including square, rectangular, elliptical, circular or other geometries. It will be understood that the shape and area of the wound-facing surface may be customized to the location and type of wound onto which the dressing is to be applied.

In various embodiments, the dressings comprise one or more additional layers 3, 4, also comprising sheet-form compositions. Such additional layers may perform any of a variety of functions in the dressings, including adherence of the absorbent layer to the wound or to surrounding tissues, increasing structural rigidity of the dressing, protection of the absorbent layer from contact with moisture or other materials in the environment in which the dressing is used, protection of a wound surface, eliminating or controlling transport of microbes from the wound (such as from the wound to the absorbent layer), and effecting delivery of actives or other materials to the wound surface. In various embodiments such additional layers are conformable to the wound surface and surrounding tissues, for example, being capable of bending such that the wound-facing surfaces of the dressing are in substantial contact with the wound and surrounding tissues.

In particular, with further reference to FIG. 1, the wound dressings 1 comprise a top sheet 3 having a wound-facing surface 7 and a back surface, such that the wound-facing surface of the absorbent structure 2 is proximate to the back surface of the top sheet 3. As discussed above, the top sheet 3 modulates exposure of the absorbent structure 2 to fluids present at the wound site when used in a method of the present technology. Accordingly, the top sheet is preferably permeable to wound fluids such as blood and wound exudate, allowing such fluids to contact the absorbent structure. In some embodiments (as generally exemplified in FIG. 1), the top sheet 3 is perforated, having a pore size that excludes passage of bacteria and other microbes. In some embodiments, the top sheet comprises plurality of pores having an average pore size larger than about 200 μm and smaller than about 3000 μm. In various embodiments, the top sheet thickness is in the range of from about 100 μm to about 1000 μm.

In some embodiments, the wound dressing further comprises a bottom sheet 4 having a wound-facing surface 6 and an opposite back surface. The bottom sheet 4 may support the absorbent structure 2 on the wound-facing surface of the bottom sheet, such that the bottom surface of the absorbent structure 2 is proximate to the wound-facing surface of the bottom sheet 4. In some embodiments, the back surface of the absorbent structure 2 is in contact with, preferably adhered to, the wound-facing surface of the bottom sheet 4.

Preferably, the bottom sheet is substantially liquid-impermeable, although permeable to water vapor. Accordingly, in some embodiments, the bottom sheet is not permeable to liquid water or wound exudate. Suitable bottom sheets will preferably have a moisture vapor transmission rate (MVTR) of the bottom sheet alone of 300 to 5000 g/m$^2$/24 hrs, preferably 500 to 2000 g/m$^2$/24 hrs at 37.5° C. at 100% to 10% relative humidity difference. Preferably, the bottom sheet is also microorganism-impermeable.

Suitable polymers for forming the bottom sheet include polyurethanes and poly-alkoxyalkyl acrylates and methacrylates. In various embodiments, the bottom sheet comprises a continuous layer of a high density blocked polyurethane foam that is predominantly closed-cell. Bottom sheet materials among those useful herein are disclosed in U.S. Pat. No. 3,645,835, Hodgson, issued Feb. 29, 1972, incorporated by reference herein. A suitable bottom sheet material is the polyurethane film commercially available as Estane® 5714F (sold by The Lubrizol Corporation).

In some embodiments, the bottom sheet comprises a resorbable polysaccharide, such as is used in the top sheet discussed above. In some embodiments, the top sheet and bottom sheet have essentially identical chemical compositions, e.g., both comprising chitosan.

In various embodiments, the bottom sheet thickness is in the range of from about 10 μm to about 1000 μm, or from about 100 μm to about 500 μm. The surfaces of the bottom sheet may have a size and configuration such that an area of the bottom sheet extends beyond the absorbent structure, i.e., wherein the bottom sheet defines a marginal region extending from about 0.5 to about 60 mm, or from about 1 mm to about 50 mm, beyond one or more edges of the absorbent layer. The absorbent layer may be characterized as an "island" on the bottom sheet. In various embodiments, the marginal region of the bottom sheet (i.e., on the wound-facing surface of the bottom sheet) is coated with an adhesive. Thus, when applied to a wound tissue, the marginal area may be used to adhere the dressing to tissues surrounding the wound.

Adhesives among those useful here include those known in the art, such as pressure sensitive adhesives. In various embodiments, the adhesive is a sensitive adhesive based on acrylate ester copolymers, polyvinyl ethyl ether, and polyurethane. Pressure sensitive adhesives among those useful herein are disclosed in U.S. Pat. No. 3,645,835, Hodgson, issued Feb. 29, 1972, incorporated by reference herein. The basis weight of the adhesive layer may be, for example, from about 20 g/m$^2$ to about 250 g/m$^2$, or from about 50 g/m$^2$ to about 150 g/m$^2$.

In some embodiments, in reference to FIG. 2, a wound dressing 10 comprises a top sheet 11 and bottom sheet 12, and absorbent structure 13. Both the top sheet 11 and the bottom sheet 12 have a size and configuration such that an area of each sheet extends beyond the absorbent structure 13, i.e., wherein the top sheet 11 defines a marginal region 14 extending from about 0.5 mm to about 60 mm, or from about 1 mm to about 50 mm, beyond one or more edges of the absorbent structure 13, and where the bottom sheet 12 defines a marginal region 14 extending from about 0.5 mm to about 60 mm, or from about 1 mm to about 50 mm, beyond one or more edges of the absorbent structure 13. The top sheet 11 and bottom sheet 12 may be adhered in the marginal region 14, e.g., by heat sealing or use of adhesive, to substantially encapsulate the absorbent structure 13.

The wound dressings are preferably sterile and packaged in a microorganism-impermeable container.

Methods of Use

The present technology provides methods of treating a wound, comprising applying to the wound a wound dressing composition, preferably as a component of a wound dressing, as described above. The compositions and dressings may be used with any of a variety of wounds, such as those occurring from trauma, surgery or disease. For example, such wounds may be chronic wounds venous ulcers, decubitus ulcers or diabetic ulcers.

Without limiting the structure or function of the wound dressings of the present technology, in various embodiments the dressings serve to modulate the activity of destructive enzymes (e.g., matrix metalloproteases (MMPs) and elastase) that can cause damage to newly formed tissue, can cause additional tissue damage, and can disrupt key signaling proteins essential to healing. In addition, in some embodiments, compositions comprising collagen can promote healing processes such as cell migration into the wound and proliferation of cells within the wound area.

The dressing when applied to the wound is hydrated by the exudate or fluid produced by the wound at which point the dry absorbent structure gels. The dressing then proceeds to breaks down and is bioresorbed (i.e. dressing does not require removal from the wound) over a period of time. This process may occur at different rates depending on the wound conditions, with residency time in the wound largely dictated by level of wound fluid production.

Moreover, in various embodiments, the wound dressings of the present technology reducing the rate of breakdown of the bioresorbable sponge material (e.g., ORC and collagen mixtures). This is achieved through isolation of the bioresorbable sponge from wound tissue fluids by the top sheets, e.g., by encapsulation of the bioresorbable sponge in a perforated bioresorbable envelope that degrades at a slower rate compared to the bioresorbable sponge material by itself. This may facilitate longer intervals for replacement of the wound dressing than are possible with dressings among those known in the art. In addition the perforations in the top sheet allow the bioresorbable sponge to modulate processes within the wound prior to complete degradation of the top sheet material.

Example

Embodiments of the present technology are further illustrated through the following non-limiting example.

A wound dressing of the present technology was made using two square films comprising about 1.5% chitosan. The films were perforated, then heat sealed down three sides to form a pocket. A bioresorbable sponge comprising ORC and collagen, having dimensions of about 3 cm by 3 cm, was inserted into the pocket. The fourth side of the chitosan films was heat sealed, thus encapsulating the ORC/collagen bioresorbable sponge.

As depicted in FIG. 3, the wound dressing 20 of the present technology was incubated with simulated wound fluid containing bacterial collagenase at a concentration of about 0.1 mg/ml for about 40 minutes at 37° C., with agitation. An ORC/collagen bioresorbable sponge control 21, having an identical composition and dimensions to the wound dressing of the present technology, but without the encapsulating chitosan sheets, was also incubated in the simulated wound fluid under the same conditions. The samples of the wound dressing and the ORC/collagen bioresorbable sponge control were visually assessed every ten minutes to ascertain the level of degradation, over a period of 40 minutes.

After 40 minutes, the wound dressing 22 of the present technology was intact, with no delamination of the sealed edges of the chitosan sheets. The ORC/collagen bioresorbable sponge 23 of the wound dressing was gelled, but still visible. However, the ORC/collagen bioresorbable sponge control 24 (i.e., without the encapsulating chitosan sheets) had completely broken down by 20 minutes, without no material visible in the solution.

Accordingly, the wound dressings of the present technology, comprising an ORC/collagen bioresorbable sponge encapsulated in a chitosan envelope, exhibited a significantly reduced rate of ORC/collagen degradation relative to similar structures not having a chitosan envelope. The wound dressings of the present technology remained intact (i.e., the heat sealed edges did not delaminate), while the perforations in the chitosan films allowed sufficient fluid to reach the ORC/collagen bioresorbable sponge so that it could gel.

Non-Limiting Discussion of Terminology

The headings (such as "Background" and "Brief Summary") and sub-headings used herein are intended only for general organization of topics within the present disclosure, and are not intended to limit the disclosure of the technology or any aspect thereof. In particular, subject matter disclosed in the "Background" may include novel technology and may not constitute a recitation of prior art. Subject matter disclosed in the "Brief Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition or method.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Components may be also be combined or eliminated in various configurations for purposes of sale, manufacture, assembly, or use. Specific examples are provided for illustrative purposes of how to make and use the compositions and methods of this technology and, unless explicitly stated otherwise, are not intended to be a representation that given embodiments of this technology have, or have not, been made or tested. Equivalent changes, modifications and variations of some embodiments, materials, compositions and methods can be made within the scope of the present technology, with substantially similar results.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Moreover, descriptions of various alternatives using terms such as "or" do not require mutual exclusivity unless clearly required by the context, and the indefinite articles "a" or "an" do not limit the subject to a single instance unless clearly required by the context.

As used herein, the words "preferred" or "preferable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

The example embodiments may also be described herein with reference to spatial relationships between various elements or to the spatial orientation of various elements depicted in the attached drawings. For example, such relationships or orientations as "top" or "bottom" assume a frame of reference consistent with an exemplary special orientation of a wound dressing. However, as would be recognized by those skilled in the art, this frame of reference is merely a descriptive expedient rather than a strict prescription as to the orientation of any given dressing as manufactured or used.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A wound dressing comprising
a bioresorbable sponge having a wound-facing surface and an opposite bottom surface, the bioresorbable sponge comprising oxidized regenerated cellulose (ORC) and collagen; and
a bioresorbable top sheet covering the wound-facing surface of the bioresorbable sponge, the top sheet comprising a polysaccharide polymer, the top sheet further comprising a perforation density of about $4/cm^2$, and the perforations have an average diameter of from about 0.02 cm to about 0.4 cm.

2. The wound dressing according to claim 1, wherein the polysaccharide polymer is selected from the group consisting of alginates, chitosan, chitin, guar gums, starch derivatives, cellulose derivatives, glycosaminoglycans, chondroitin sulfate, heparin sulfate, and a mixture of any two or more thereof.

3. The wound dressing according to claim 1, wherein an aqueous solution used to generate the top sheet has a solids content of from about 1% wt./vol. to about 5% wt./vol.

4. The wound dressing according to claim 1, further comprising a bottom sheet.

5. The wound dressing according to claim 4, wherein the bottom sheet comprises a resorbable polysaccharide.

6. The wound dressing according to claim 4, wherein the top sheet and the bottom sheet are bonded so as to substantially encapsulate the bioresorbable sponge.

7. The wound dressing according to claim 1, wherein the bioresorbable sponge further comprises a structural protein.

8. The wound dressing according to claim 7, wherein the structural protein is selected from the group consisting of fibronectin, gelatin, fibrin, laminin, elastin, and a mixture of any two or more thereof.

9. The wound dressing according to claim 7, wherein the bioresorbable sponge comprises at least 75% of a mixture of the ORC and the structural protein by weight.

10. The wound dressing according to claim 1, wherein the bioresorbable sponge comprises a mixture of ORC and collagen, wherein the mixture comprises from about 50% to about 60% collagen by weight.

11. The wound dressing according to claim 1, wherein the bioresorbable sponge is substantially planar, having a width of from about 3 cm to about 30 cm, and a length of from about 3 cm to about 30 cm.

12. The wound dressing according to claim 1, further comprising an antimicrobial agent selected from the group consisting of tetracyclines, beta-lactams, macrolides, aminoglycosides, fluoroquinolones, silver, silver salts, and a mixture of any two or more thereof.

* * * * *